United States Patent [19]

Engle et al.

[11] 4,342,318
[45] Aug. 3, 1982

[54] PHYSIOLOGICAL WAVEFORM PROCESSOR

[75] Inventors: William R. Engle, Blaine, Minn.; Ronald H. Rockland, Parsippany, N.J.

[73] Assignee: Medtronic, Inc., Minneapolis, Minn.

[21] Appl. No.: 180,710

[22] Filed: Aug. 25, 1980

[51] Int. Cl.³ .............................................. A61B 5/04
[52] U.S. Cl. ................................................... 128/708
[58] Field of Search ............... 128/702, 703, 704, 708, 128/705, 706

[56] References Cited

U.S. PATENT DOCUMENTS

| | | | |
|---|---|---|---|
| 3,606,882 | 9/1971 | Abe et al. | 128/703 |
| 3,611,164 | 10/1971 | Day | 128/704 |
| 3,698,386 | 10/1972 | Fried | 128/705 |
| 3,878,833 | 4/1975 | Arneson | 128/708 |
| 3,902,479 | 9/1975 | Chaumet | 128/703 |
| 3,946,725 | 3/1976 | Bolshov et al. | 128/706 |
| 4,250,881 | 2/1981 | Grosskopf | 128/702 |

Primary Examiner—William E. Kamm

Attorney, Agent, or Firm—Schroeder, Siegfried, Vidas, Steffey & Arrett

[57] ABSTRACT

Apparatus for processing waveform signals of physiological origin. The apparatus includes circuitry for developing a signal representative of the peak-to-peak amplitude between each waveform signal peak and the next successive waveform signal peak as well as circuitry for developing a signal representative of the slew rate of the waveform signal between successive waveform signal peaks. In a preferred embodiment, developed signals are stored in resettable memories, the memories being reset on the occurrence of a sign or polarity change in the slope of the waveform signal. Sampling circuitry is provided for establishing a maximum peak-to-peak amplitude within the waveform signal as well as its associated slew rate. Within the context of an ECG, the maximum peak-to-peak amplitude and associated slew rate represent the QRS complex and the apparatus of the present invention may be employed within a pacemaker as a sense amplifier. Alternatively, the apparatus of the present invention may be employed to determine whether or not a pacing lead is properly placed and the pacemaker is suitable for application to the patient.

9 Claims, 8 Drawing Figures

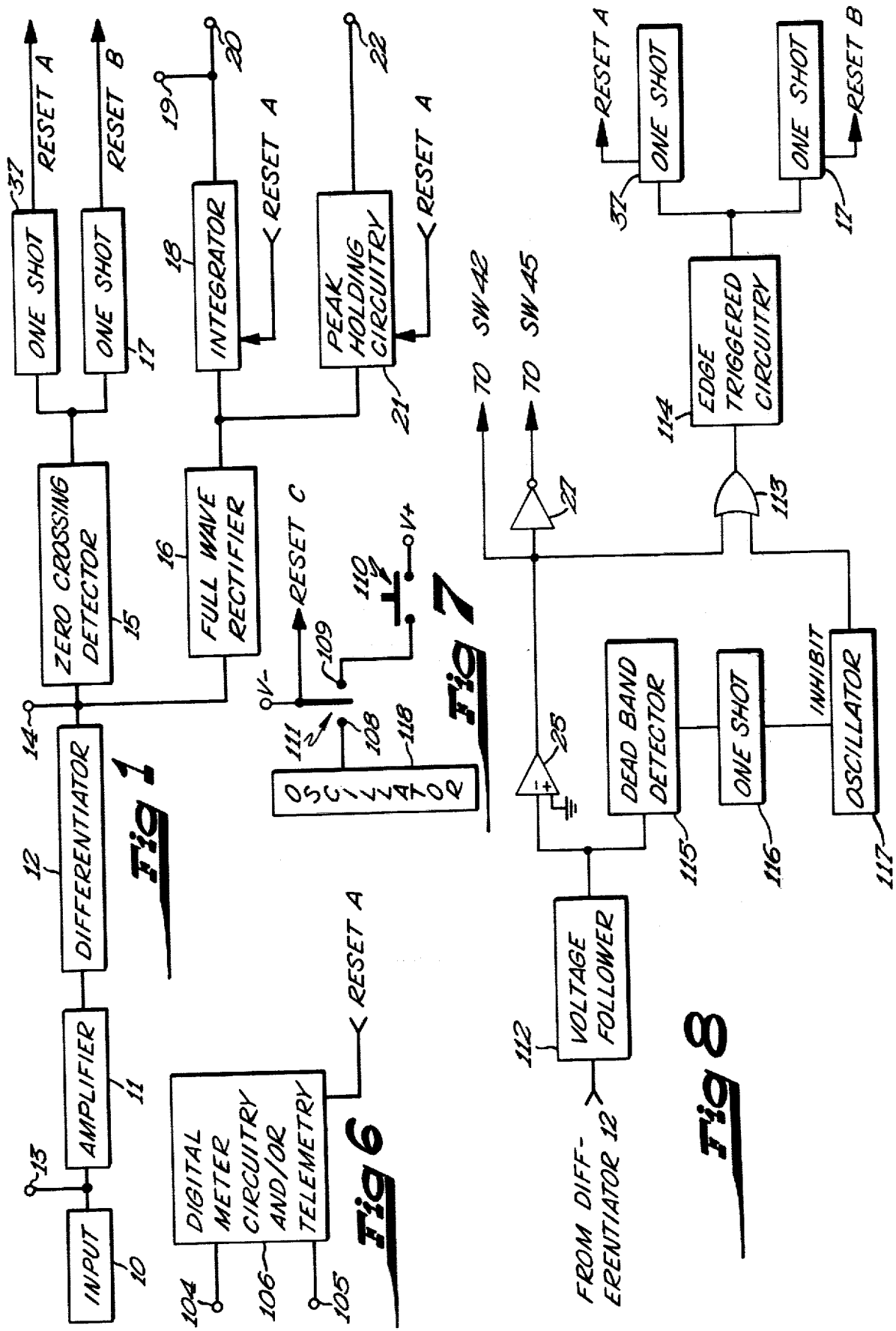

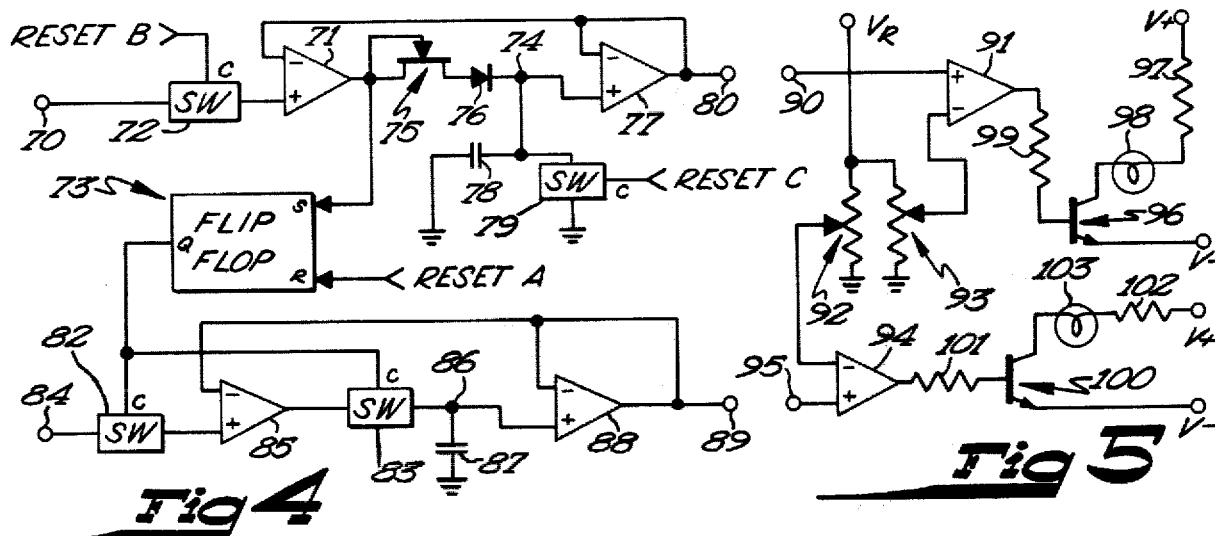
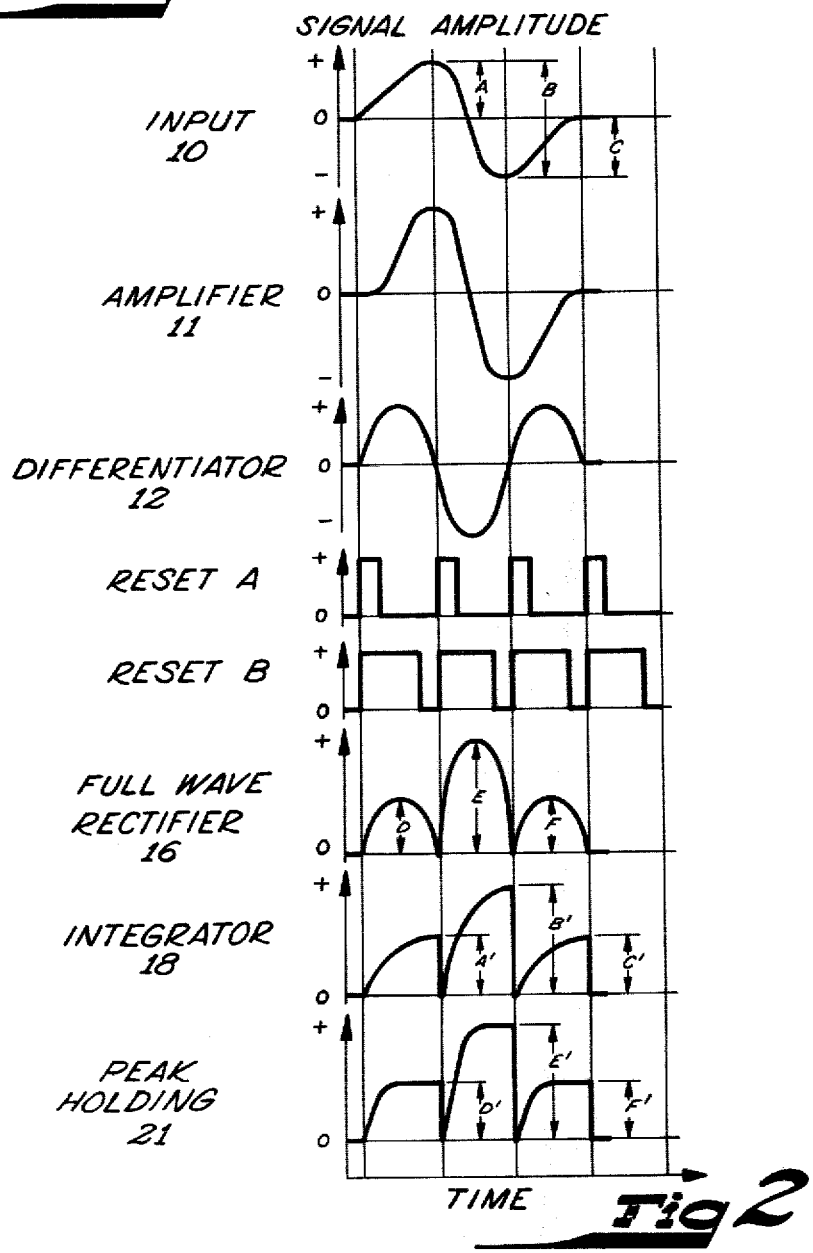

PHYSIOLOGICAL WAVEFORM PROCESSOR

DESCRIPTION

Background of Prior Art

Physiological waveform processors are known to the prior art for such purposes as detecting the occurrence of a particular waveform characteristic. For example, such devices have been used to detect the occurrence of an R-wave or a QRS complex within an ECG.

Typical prior art devices of the type described recognize that the slope or slew rate of the waveform characteristic of interest often differs from that of the remainder of the waveform. When the characteristic of interest has a greater slew rate than other waveform characteristics, a mere comparison of the derivative of the waveform signal against a reference value can reliably detect the occurrence of the characteristic of interest. In an environment where noise or other extraneous signals are likely to be present, a second criterion may be employed to reduce the probability of a false indication of the waveform characteristic of interest.

A prior art device which employs the slope or slew rate of a waveform to detect the occurrence of a particular waveform characteristic is shown in U.S. Pat. No. 3,878,833, issued Apr. 22, 1975, for PHYSIOLOGICAL WAVEFORM DETECTOR. The referenced patent includes an embodiment which detects the occurrence of the QRS complex in an ECG waveform essentially by comparing the derivative of the waveform signal with a reference signal and determining whether the derivative signal exceeds the reference signal for a predetermined period of time. Thus, two criteria are employed to detect the QRS complex; namely, magnitude and duration. The magnitude criterion distinguishes between the QRS complex and other portions of the ECG as well as low frequency artifacts and noise. The duration criterion distinguishes between the QRS complex and muscle spikes, pacemaker pulses and other high frequency artifacts.

Prior art devices of the type disclosed in the referenced patent can detect a QRS complex in an ECG and other waveform characteristics within other waveforms. The process of detection by comparison with a reference value, however, merely gives an indication of the occurrence of the characteristic of interest without any indication as to the parameters of the characteristic. Further, the criteria employed by the prior art may not be the most reliable or dedirable to establish the occurrence of the characteristic. For example, in determining whether or not a cardiac pacing lead is properly placed, a comparison of the maximum peak-to-peak amplitude and its associated slew rate to reference values may be far more valuable than the magnitude and duration of a waveform characteristic.

Brief Summary of the Invention

Briefly described, the present invention provides apparatus for processing waveform signals of physiological origin including circuitry for developing a signal representative of the peak-to-peak amplitude between each waveform signal peak and the next successive signal peak as well as circuitry for developing a signal representative of the slew rate of the waveform signal between successive waveform signal peaks. Circuitry is also provided for establishing the maximum peak-to-peak amplitude of the waveform signal and its associated slew rate. Thus, the present invention allows an analysis of the peak-to-peak amplitude and slew rate of a waveform signal having a physiological origin and may also be employed to detect the occurrence of a particular waveform characteristic as by comparing the peak-to-peak amplitude and its associated slew rate against reference values. In the latter case, detection of the waveform characteristic may be for the purpose of establishing that the characteristic has, in fact, occurred or to test the reliability of the interconnection between the body and the waveform processor. For example, comparison of the maximum peak-to-peak amplitude, and its associated slew rate, against reference values may be employed to detect the occurrence of a QRS complex in an ECG waveform, as in a sense amplifier a cardiac pacemaker, or to check the lead placement for a cardiac pacemaker.

BRIEF DESCRIPTION OF THE DRAWINGS

FIG. 1 illustrates a portion of the apparatus of the present invention.

FIG. 2 illustrates the operational characteristics of that portion of the invention illustrated in FIG. 1.

FIG. 4 illustrates an additional apparatus forming a portion of the present invention.

FIG. 5 illustrates still another additional portion of the apparatus of the present invention.

FIG. 6 illustrates alternative apparatus to the illustrated FIG. 5.

FIG. 7 illustrates additional apparatus forming a portion of the present invention.

FIG. 8 illustrates alternative apparatus to a portion of that illustrated in FIGS. 1 and 3.

DETAILED DESCRIPTION OF INVENTION

Figure 3:
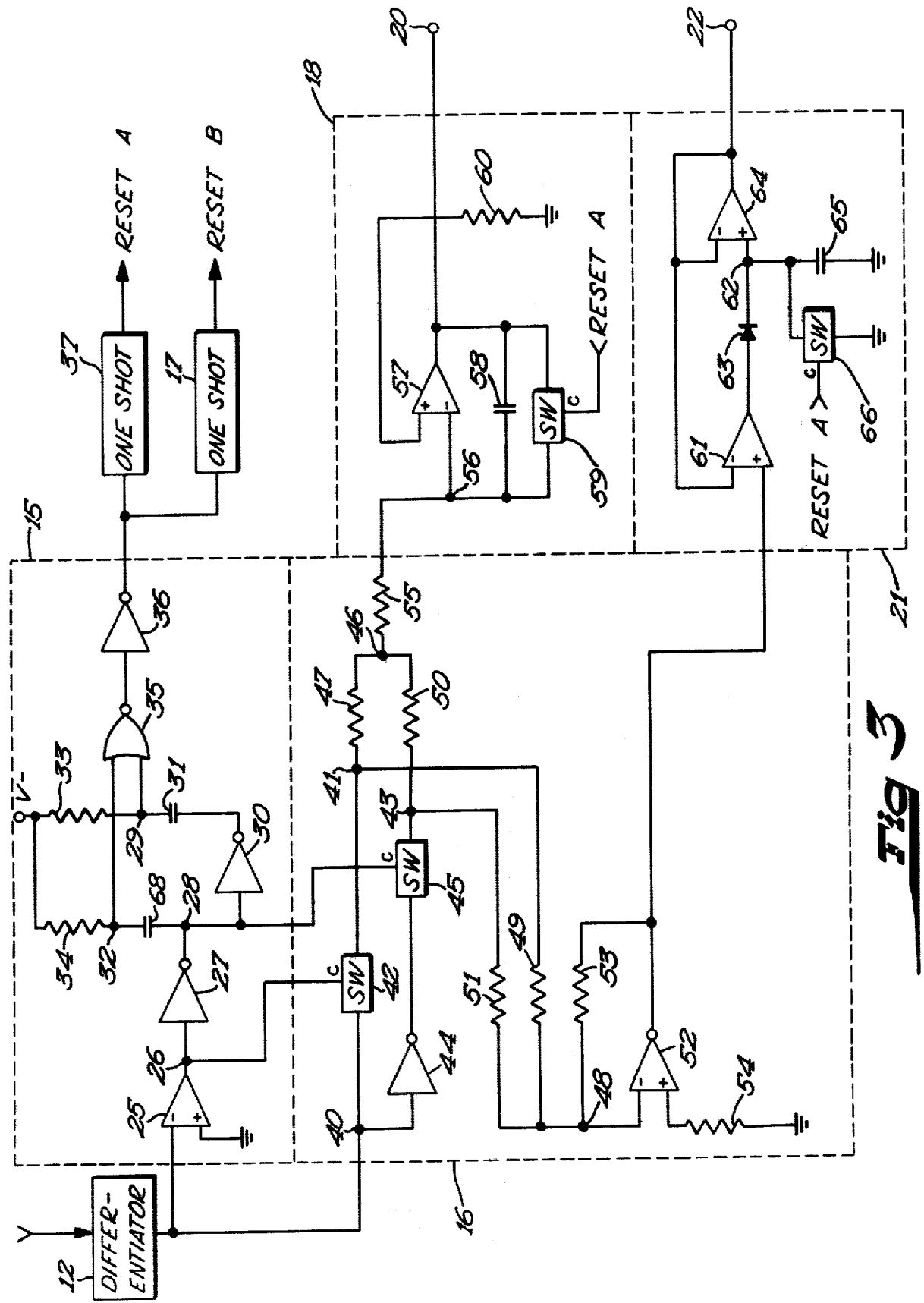
FIG. 3 is a schematic drawing of a portion of the apparatus illustrated in FIG. 1.

Referring now to FIG. 1, there is shown a portion of a preferred embodiment of the present invention including an input 10. The input 10 is adapted to receive a waveform signal to be processed and may therefore include appropriate electrodes. Alternatively, the input 10 may be adapted for connection to appropriate receiving electrodes such as ECG electrodes or cardiac pacemaker sensing electrodes or may be adapted to receive recorded data for analysis. The input 10 is connected to an amplifier 11 which has its output connected to a differentiator 12. A junction 13 may be connected intermediate the input 10 and amplifier 11 and a second junction 14 may be connected to the output of differentiator 12, the functions of junction 13 and 14 being more fully described below. The output of differentiator 12 is applied to the input of a zero crossing detector 15 and to the input of a full wave rectifier 16. The output of the zero crossing detector 15 triggers one shots 37 and 17 whose outputs appear as signals "Reset A" and "Reset B," respectively. The output of the full wave rectifier 16 is applied to an integrator 18 whose output is applied to terminals 19 and 20 and to a peak holding circuit 21 whose output is applied to a terminal 22. As will be explained more fully below, integrator 18 and peak holding circuit 21 are connected to be reset by the "Reset A" signal. The amplifier 11 and differentiator 12 may be the type having low-frequency and high-frequency rolloff to assist in eliminating noise from their output signals. Differentiator 12 has a limited frequency response to serve a "smoothing" function to even out "glitches" or notches in the waveform being processed to reduce the possibility that such notches will be recognized as a characteristic of the waveform, or a part thereof.

Referring now to FIG. 2, there is shown a graphic illustration of a signal applied to the input 10 and the corresponding output signal of the several components illustrated in FIG. 1. The signal appearing at input 10 may represent a QRS complex of a cardiac waveform. The signal from input 10 is amplified by amplifier 11 which is merely a gain amplifier and differentiated by differentiator 12. The zero crossing detector 15 detects each approach toward and/or departure from zero of the differentiator signal, from both positive and negative directions, and triggers one shots 17 and 37 to produce a "Reset A" and "Reset B" signal on each such approach and/or departure, in known manner. One shots 17 and 37 are retriggerable one shots. The function of the "Reset B" signal will be discussed more fully below with reference to FIG. 4. The signal from differentiator 12 is passed through full wave rectifier 16 whose output represents the absolute value of the differentiator signal. The output signal from the full wave rectifier 16 is integrated by the integrator 18 and applied to a peak holding circuit 21, each of which has a memory which will be described more fully with reference to FIG. 3. The memory of integrator 18 stores the value of the integral of the full wave rectifier 16 output with the peak holding memory storing the maximum value represented by the signal from the full wave rectifier 16. The memories of the integrator 18 and peak holding circuit 21 are each reset by the "Reset A" signals (on each change of sign or polarity of the output signal of differentiator 12). Thus, on the occurrence of each "Reset A" signal, the value of the integrator 18 output signal represents the peak-to-peak amplitude of the signal applied to the input 10, as illustrated by the arrows A, B, C and A', B', C'. Also, on the occurrence of each "Reset A" signal, the value stored in the memory of peak holding circuit 21 represents the maximum value of the output signal of full wave rectifier 16 as illustrated by arrows D, E, F and D', E', F', which values represent the slew rate or slope of the signals applied to the input 10.

Referring now to FIG. 3, there is shown a schematic of zero crossing detector 15, full wave rectifier 16, integrator 18 and peak holding circuit 21 and their interconnection with the differentiator 12, junctions 20 and 22 and "Reset A" signal. The junction 19 does not appear in FIG. 3 and will be described more fully below. The zero crossing detector 15 includes a comparator formed of an open-loop, high-gain amplifier 25 which receives the output signal from the differentiator 12 on its non-inverting input terminal and has its inverting input terminal grounded. Unless specifically stated otherwise, all amplifiers disclosed herein are open-loop, high-gain amplifiers. The output of amplifier 25 is applied to a junction 26 and to an inverter 27 which is connected between the amplifier 25 and a junction 28. The junction 28 is connected to a junction 29 via inverter 30 and capacitor 31 and to a junction 32 via capacitor 68. A negative voltage (V−) supply, such as batteries, is connected to the junction 29 via resistor 33 and to junction 32 via resistor 34. The junctions 29 and 32 are connected to different inputs of a NOR gate 35, the output of NOR gate 35 being applied to an inverter 36 whose output triggers one shot 37 to provide the "Reset A" signal.

In operation, the amplifier 25 functions as a comparator in known fashion. Its output is applied to the junction 26 and is inverted by inverter 27 and is applied to junction 28. The capacitor 68 and resistor 34 function as a positive-edge trigger operating on signals appearing at the junction 28 while the capacitor 31 and resistor 33 function as a negative-edge trigger by virtue of the inversion of the signal at junction 28 by inverter 30. The positive-edge and negative-edge signals are combined at NOR gate 35 and inverted at inverter 36 to trigger the "Reset A" signal on the occurrence of each approach toward zero of the differentiator 12 output signal.

The output signal of differentiator 12 is applied to the full wave rectifier 16 at a junction 40. The junction 40 is connected to a junction 41 by an electronic switch 42 whose control electrode is connected to the junction 26 of zero crossing detector 15. The junction 40 is also connected to a junction 43 via inverter 44 and electronic switch 45, the control electrode of switch 45 being connected to junction 28 of zero crossing detector 15. The junction 41 is connected to a junction 46 via resistor 47 and to a junction 48 via resistor 49. Similarly, the junction 43 is connected to the junction 46 via resistor 50 and to the junction 48 via resistor 51. The junction 48 is connected to the inverting input terminal of an amplifier 52 and to the output terminal of the amplifier 52 via resistor 53. The non-inverting input terminal of amplifier 52 is connected to ground through a resistor 54.

Because of the inverted relationship between the junctions 26 and 28, one of switch 42 and switch 45 will be on while the other is off. On a change in sign in the input signal to comparator 25, the conducting switch will go off while the other will conduct. Additionally, the action of the inverter 44 in combination with the alternate conduction of switch 42 and switch 45 results in a signal at the junction 46 representative of the absolute value of the signal applied to the junction 40. The amplifier 52 and associated circuitry functions as a summing amplifier, in known manner, whose output corresponds to the absolute value signal appearing at junction 46, the amplifier 52 providing isolation between the signals to be applied to the integrator 18 and peak holding circuit 21. In the illustrated embodiment the output signal from amplifier 52 is of opposite polarity from the signal at junction 46, the signal at junction 46 corresponding to an inverted absolute value signal. Zero crossing detectors and full wave rectifiers are known to the prior art and embodiments thereof are illustrated and briefly discussed herein for the purpose of clarity of presentation.

The signal appearing at the junction 46 is passed to the integrator 18 through resistor 55 and is applied to a junction 56. The junction 56 is connected to the inverting input of an amplifier 57 and to the output of the amplifier 57 by a parallel connected capacitor 58 and electronic switch 59, the control electrode of switch 59 being connected to receive the "Reset A" signal. The non-inverting input of amplifier 57 is connected to ground by a resistor 50 and the output of the amplifier 57 is connected to the terminal 20. In operation, the capacitor 58 is charged to a level representative of the integral of the input to the integrator 18 from rectifier 16, in known manner, and in that capacity may be viewed as providing a memory function. The capacitor 58 is discharged or "reset" on the appearance of each "Reset A" signal which renders the switch 59 conductive. Integrators are known to the prior art and an embodiment thereof is illustrated and briefly discussed for the purpose of clarity and to illustrate the memory capability and reset function of the illustrated embodiment.

Peak holding circuits are also known to the art and an embodiment of one is illustrated and briefly discussed herein for the purpose of clarity and to illustrate the memory capability and reset function of the illustrated embodiment. The output of amplifier 52 of full wave rectifier 16 is applied to the non-inverting input of an amplifier 61. The output of amplifier 61 is connected to a junction 62 via a diode 63. The junction 62 is connected to the non-inverting input of an amplifier 64 and to ground via parallel connected capacitor 65 and electronic switch 66. The control electrode of electronic switch 66 is connected to receive the "Reset A" signal. The output of the amplifier 64 is connected to the terminal 22, to the inverting input terminal of amplifier 64 and to the inverting input terminal of the amplifier 61. In operation, the capacitor 65 will charge to a value representative of the maximum value applied to the non-inverting input of amplifier 61. That value will also appear at the terminal 22 and the capacitor 65 is reset on each occurrence of a "Reset A" signal at the control electrode of switch 66.

Referring now to FIG. 4, there is shown a circuit especially adapted for connection to the circuit of FIGS. 1 and 3 which will provide an output signal representative of the maximum peak-to-peak amplitude of the signal applied to the input 10 and the maximum slew rate that occurred during said maximum peak-to-peak amplitude—the maximum peak-to-peak amplitude being illustrated by the arrows B in the waveforms shown in FIG. 2. The terminal 70 is connected to the non-inverting input of an amplifier 71 through an electronic switch 72, the control electrode of switch 72 being connected to receive the "Reset B" signal. The output of the amplifier 71 is connected to the set terminal of a flip-flop 73, to a junction 74 through a FET 75 and a diode 76 and to the gate electrode of FET 75. FET 75 provides a back-up in the event of leakage of diode 76. The junction 74 is connected to the non-inverting input of an amplifier 77 and to ground via parallel connected capacitor 78 and electronic switch 79. The output of the amplifier 77 is connected to its inverting input and to the inverting input of amplifier 71.

With the exception of flip-flop 73, the circuitry of FIG. 3 discussed to this point constitutes a maximum peak memory. The terminal 70 is adapted for connection to the terminal 20 to receive the output signals from the integrator 18. Switch 72 blocks the signals of integrator 18 from the remainder of the circuitry of FIG. 4 except during the occurrence of a "Reset B" signal. Thus, only during the occurrence of a "Reset B" signal will a signal applied to terminal 70 be applied to the input of amplifier 71. The duration of the "Reset B" signal is established by one shot 17 (see FIGS. 1 and 3). It is presently contemplated that a "Reset B" signal of 50 ms duration is suitable for use within the apparatus of the present invention for operation with cardiac waveforms as 50 ms approximates the time between peaks in the QRS complex and the termination of the "Reset B" signal after 50 ms terminates the processing of waveforms in the circuitry of FIG. 4 having a greater peak-to-peak interval.

Assuming a charge on capacitor 78 and no "Reset C" signal applied to the control electrode of switch 79, the value of that charge will appear at terminal 80 and be applied to the inverting input terminals of amplifiers 71 and 77. A signal appearing at terminal 70, during a "Reset B" signal, having a value smaller than the charge value of capacitor 78 will result in a negative output from amplifier 71 leaving FET 75 non-conductive. In this non-conductive state FET 75 is functionally an "open circuit" thus leaving the charge on capacitor 78 unchanged. Diode 76 serves as a redundant system to maintain the charge of capacitor 78 unchanged under the conditions stated to this point. Theoretically only diode 76 is required.

On the appearance of a signal at terminal 70, during a "Reset B" signal, having a value greater than a charge value of capacitor 78, the output of amplifier 71 is positive, FET 75 is rendered conductive and capacitor 78 will charge until its charge value corresponds to the value of the signal appearing on terminal 70, the charge value of capacitor 78 appearing at terminal 80. With capacitor 78 charged to a value corresponding to the value of the signal at terminal 70, the output of amplifier 71 will again go negative to render switch 75 non-conductive. Thus, capacitor 78 will charge to a value representative of the maximum value applied to the terminal 70 during a "Reset B" signal period and hold that value until reset or a signal having a greater value is applied to terminal 70. With reference to FIG. 2, capacitor 78 will charge to a value representative of arrow A′ in the output signal of integrator 18, will increase its charge to a value representative of the arrow B′ and will hold that value during the occurrence of a signal having a value indicated by the arrow C′. Inasmuch as the arrow B′ is representative of a maximum peak-to-peak amplitude of the signal applied to the input 10 (arrow B) the circuitry of FIG. 4 discussed to this point will detect the maximum peak-to-peak amplitude of a waveform being processed and will hold a value representative of that amplitude in a memory formed by capacitor 78. Capacitor 78 may be periodically reset by rendering switch 79 conductive as with a "Reset C" signal whose generation will be described below.

The Q-terminal of flip-flop 73 is connected to the control electrodes of electronic switches 82 and 83. Switch 82 interconnects a terminal 84 and the non-inverting input terminal of an amplifier 85. Switch 83 interconnects the output of amplifier 85 and a junction 86. The junction 86 is connected to ground through a capacitor 87 and to the non-inverting input terminal of an amplifier 88. The output of amplifier 88 is connected to its inverting input terminal and to the inverting input terminal of amplifier 85 as well as to a terminal 89. The terminal 84 is adapted for connection to the terminal 22 of peak holding circuit 21.

During the time that FET 75 is rendered conductive (when the output of amplifier 71 is positive) flip-flop 73 is set and its Q output goes high. That is, during the occurrence of a "Reset B" signal and a signal applied to terminal 70 having a value greater than the charge value of capacitor 78, a set signal is applied to the set terminal of flip-flop 73 and its Q output goes high. In this state, switches 82 and 83 are rendered conductive. With switches 82 and 83 conductive, a signal appearing at terminal 84 will affect the charge value of the capacitor 87. For example, a signal to terminal 84 having a value greater than the charge value of capacitor 87 will result in capacitor 87 charging to the value of the signal applied to the terminal 84. Conversely, a signal applied to terminal 84 having a value lower than the charge value of capacitor 87 will result in a negative output from amplifier 85 and a discharge of capacitor 87 through switch 83. Thus, the charge of capacitor 87 will be representative of the value of the signal applied to the terminal 84 during conduction of switches 82 and 83 and that charge value will be applied to the output terminal 89. With the switches 82 and 83 non-conductive, the charge value of capacitor 87 will be maintained without regard to the value of any signal appearing at the terminal 84.

As described above, the charge value of capacitor 78 and signal at terminal 80 represents the maximum peak-to-peak amplitude experienced in the waveform being processed to that point in time. On the occurrence of a greater peak-to-peak amplitude, the charge value of capacitor 78 is increased and appears at terminal 80. During the time that capacitor 78 is charging, flip-flop 73 is set rendering switches 82 and 83 conductive and causing the charge value of capacitor 87 to increase or decrease in accordance with its relationship to the value of the signal applied to terminal 84. Since the terminal 84 is connected to a terminal 22, the capacitor 87 will charge or discharge to a value representative of the maximum slew rate associated with the maximum peak-to-peak amplitude experienced in the waveform being processed to that point in time. On the occurrence of a "Reset C" signal, capacitor 78 is discharged and will recharge to a value representative of the next peak-to-peak amplitude, and subsequent, greater, peak-to-peak amplitudes. Thus, after a "Reset C" signal, the charge value of capacitor 78 represents the maximum peak-to-peak amplitude experienced in the waveform after the "Reset C" signal and the charge value of capacitor 87 represents the maximum slew rate associated with that maximum peak-to-peak amplitude.

Referring now to FIG. 5, there is shown circuitry for comparing the maximum peak-to-peak amplitude and its associated slew rate against reference values for the purpose of detecting a particular waveform characteristic, a QRS complex, for example. A terminal 90 is adapted for connection to the terminal 80 to apply the signal at terminal 80 to the non-inverting input of amplifier 91. A regulated voltage supply ($V_R$) is connected to ground through potentiometers 92 and 93, the wiper arms of which are connected to the inverting input terminals of an amplifier 94 and an amplifier 91, respectively. A terminal 95 is adapted for connection to the terminal 89 for applying the signal at terminal 89 to the non-inverting input of amplifier 94. A positive supply voltage (V+) is connected to the collector of a transistor 96 through a resistor 97 and light indicator 98 while its emitter is connected to a negative power supply (V−). The output of amplifier 91 is connected to the base of transistor 96 through a resistor 99. Similarly, a transistor 100 has its base connected to amplifier 94 via resistor 101, its emitter connected directly to a negative voltage supply (V−) and its collector connected to a positive voltage supply (V+) through a resistor 102 and a light indicator 103. The light indicators 98 and 103 may be any suitable indicating lights, LED's, for example. The circuitry of FIG. 5 is known to the art and is shown to illustrate the fact that the apparatus of the present invention may be employed to detect the occurrence of a particular waveform characteristic and to indicate that occurrence in a detectable manner as by illuminating the light indicators 98 and 103. As will be apparent to those familiar with the art, the reference values against which the signals applied to terminals 90 and 95 are compared are established by the potentiometers 93 and 92, respectively. Within the QRS complex, the average maximum peak-to-peak value is on the order of 10 millivolts with the associated slew rate value being on the order of 1 volt/second.

FIG. 6 is included to illustrate the fact that the apparatus of the present invention may be combined with conventional digital meter circuitry to provide a digital readout of the amplitude and/or slew rate of the waveform being processed. As illustrated in FIG. 6, conventional rate circuitry 106 may be provided with input terminals 104 and 105. By connecting the terminal 104 to the terminal 80 and the terminal 105 to the terminal 89, the digital meter circuitry 106 will provide digital information representative of the maximum peak-to-peak amplitude and its associated slew rate. Similarly, by connecting terminal 104 to terminal 20 and terminal 105 to terminal 22 and resetting the meter circuitry on the occurrence of each "Reset A" signal, the apparatus of FIG. 6 can provide digital information regarding the peak-to-peak amplitude and associated slew rate of each peak transition. Alternatively, suitable telemetry apparatus may be included in circuitry 106 to telemeter the output data to a remote location whether displayed at 106 or not.

Referring now to FIG. 7, there is shown an oscillator 118 having its output connected to a terminal 108 and a positive power supply (V+) connected to a terminal 109 by a manual switch 100. Terminals 108 and 109 are part of a two-position switch 111 which may be selectively positioned in contact with either of the terminals 108 and 109 to provide a signal on the "Reset C" line. For example, with a switch 111 closed on terminal 108, a "Reset C" signal will be periodically produced under the control of the oscillator 118. Alternatively by placing the switch 111 on terminal 109, a "Reset C" signal will be produced only when the switch 110 is depressed. As discussed with reference to FIG. 4, the "Reset C" signal is employed to clear the memory of the maximum peak-to-peak memory, for example after the peak-to-peak amplitude of one QRS complex has been established and prior to another QRS complex. As illustrated, the "Reset C" signal is connected to a negative power supply (V−).

Referring now to FIG. 8, there is shown an alternative to the zero crossing detector 15 of FIGS. 1 and 3 which may be employed with the remainder of the circuitry of those figures. To facilitate the understanding of FIG. 8, elements having the same function as the elements of FIG. 3 are assigned the same reference numeral. A voltage follower 112 is connected to receive the output signals from the differentiator 12. The output of voltage follower 112 is connected to comparator 25 whose output is connected to switch 42 and is inverted by inverter 27 and applied to switch 45. The output of comparator 25 is also applied to an OR gate 113 whose output is applied to edge triggered circuitry 114. The output of edge triggered circuitry 114 provides the "Reset A" and "Reset B" signals via one shots 37 and 17, respectively.

With the exception of voltage follower 112 and OR gate 113 the elements of FIG. 8 discussed to this point function as discussed with reference to the zero crossing detector 15 of FIG. 3 including edge triggered circuitry 114 which is not shown in FIG. 8 in the detail shown in FIG. 3. The voltage follower 112 is merely a buffer amplifier and the function of OR gate 113 will be apparent from the following discussion.

The output of voltage follower 112 is also applied to dead band detector 115 whose output triggers a one shot 116. One shot 116 is connected to the inhibit terminal of an oscillator 117 to inhibit oscillator 117 when one shot 116 is triggered. The output of oscillator 117 is connected as an input to OR gate 113 which passes pulses from either oscillator 117 or comparator 25 to trigger edge triggered circuitry 114. Dead band detectors are known, one type being commonly referred to as a window comparator. Dead band detector 115 may be a window comparator centered at zero to provide an output signal when the absolute value of the signal from voltage follower 112 exceeds zero by a predetermined value.

The concept underlying the embodiment of FIG. 8 is the fact that slew rates below a predetermined level are not likely to be associated with any waveform characteristic of interest. For example, if the purpose is to detect a QRS complex, slew rates below a predetermined value may be ignored and, preferably, excluded from the processing circuitry. Thus, at such low slew rates the oscillator 117 will result in a series of "Reset A" signals at its oscillation frequency to continually reset portions of the apparatus, integrator 18 and peak holding circuitry 21, among others. Within a cardiac waveform processor the oscillator 117 may have an oscillation frequency of 1 KHz and the predetermined value at which dead band detector 115 provides a signal to inhibit oscillator 117 may be 0.1 volt/second.

Obviously, many modifications and variations of the present invention are possible in light of the above teachings. For example, the present invention may be assembled as disclosed for incorporation into a body implantable device, a demand cardiac pacemaker, for example, to reliably perform many of the functions of a sense amplifier. Alternatively, the apparatus of the present invention may be employed as an external unit for processing physiological waveforms. In this context, the input 10 may be provided with an isolation amplifier of known design to isolate the input electrodes from the remainder of the circuitry. Also, in the external mode, the terminals 13, 14 and 19 may be connected to buffered outputs representative of the input, amplitude and slew rate, respectively. Telemetry may also be employed with any of the output terminals to telemeter information corresponding to the signals at those terminals to a remote location. Further, the concepts of the present invention may be applied to establish the slew rate at the maximum peak-to-peak amplitude or the peak-to-peak amplitude at the maximum slew rate. It is therefore to be understood that, within the scope of the appended claims, the invention may be practiced otherwise than as specifically described.

We claim:

1. Apparatus for processing waveform signals of physiological origin including input means for receiving said waveform signals, said apparatus comprising:
   first means operatively connected to said input means for developing a signal representative of the peak-to-peak amplitude between each waveform signal peak and the next successive waveform signal peak;
   second means operatively connected to said input means for developing a signal representative of the maximum slew rate of said waveform signal between successive waveform signal peaks, said first and second means each comprising resettable memory means;
   third means operatively connected to said input means and said first and second means for generating a memory means reset signal on the occurrence of a sign change in the slope of said waveform signal;
   fourth means connected to receive said first means signal including memory means for storing said first means signal, said fourth means further comprising means for blocking all first means signals from said fourth means memory means which do not exceed the last signal stored in said memory means;
   fifth means connected to receive said second means signal including memory means for storing said second means signal; and p1 means for gating said second means signal to said fifth means memory means, said fifth means including means for enabling said gating means only on the occurrence of a first means signal that exceeds the last first means signal stored in said memory means.

2. The apparatus of claim 1 further comprising:
   sixth means operatively connected to said input input means for generating a signal of predetermined duration on the occurrence of a sign change in the slope of said waveform signal; and
   means connected to said sixth means for gating said first means signal to said fourth means under the control of said sixth means signal.

3. The apparatus of claim 2 wherein said first means signal gating means is enabled during said sixth means signal.

4. Apparatus for processing waveform signals of physiological origin including input means for receiving said waveform signals, said apparatus comprising:
   first means operatively connected to said input means for generating a signal on the occurrence of a sign change in the slope of a waveform signal;
   second means operatively connected to said input means for developing a signal representative of the peak-to-peak amplitude of each waveform peak and the next successive waveform peak; and
   third means operatively connected to said input means for developing a signal representative of the maximum slew rate of said waveform signal associated with each peak-to-peak amplitude, said second and third means being connected to said first means and responsive to said first means signal to establish predetermined initial second and third means signals on the occurrence of each first means signal.

5. The apparatus of claim 4 further comprising:
   fourth means connected to receive said second means signal including memory means for storing said second means signal; and
   fifth means connected to receive said third means signal including memory means for storing said third means signal.

6. The apparatus of claim 5 wherein said fourth means further comprises means for blocking all second means signals from said fourth means memory means which do not exceed the last signal stored in said memory means.

7. The apparatus of claim 6 further comprising means for gating said third means signal to said fifth means memory means, said fourth means including means for enabling said gating means only on the occurrence of a second means signal that exceeds the last signal stored in said fourth means memory means.

8. The apparatus of claim 7 further comprising:

sixth means operatively connected to said input means for generating a signal of predetermined duration on the occurrence of a sign change in the slope of said waveform signal; and means connected to said sixth means for gating said second means signal to said fourth means under the control of said sixth means signal.

9. The apparatus of claim 8 wherein said second means signal gating means is enabled during said sixth means signal.

* * * * *